United States Patent [19]

Cho

[11] Patent Number: 4,952,505
[45] Date of Patent: Aug. 28, 1990

[54] FERMENTATION OF TRICHODERMA REESEI AND APPARATUS THEREFOR

[75] Inventor: Michael Y. Cho, Tallahassee, Fla.

[73] Assignee: Florida State University, Tallahassee, Fla.

[21] Appl. No.: 229,823

[22] Filed: Aug. 8, 1988

[51] Int. Cl.$^5$ .......................... C12N 9/42; C12R 1/885
[52] U.S. Cl. ..................................... 435/209; 435/945
[58] Field of Search .............................. 435/209, 945

[56] References Cited

FOREIGN PATENT DOCUMENTS 133035 2/1985 European Pat. Off. ............ 435/209

OTHER PUBLICATIONS

Gallo, "Cellulase Production by the New Hyperproducing Strain of Trichoderma Reesei, MCG80", Presented at 1982 Winter National Meeting American Institute of Chem. Eng., Orlando, Fl., Feb. 28–Mar. 3.
Mandels et al., "Induction of Cellulase in Trichoderma Viride as Influenced by Carbon Sources and Metals", J. Bacteriol, 1957, vol. 73, pp. 269–278.
Mandels et al., "Enzymatic Hydrolysis of Waste Cellulose", Biotech. Bioeng., 1974, vol. 16, pp. 1471–1493.
Yayanos et al., "A Study of the Effects of Hydrostatic Pressure on Macromolecular Synthesis in Escherichia Coli", Bio-Physical Journal, 1969, vol. 9, pp. 1464–1482.
Thom et al., "Microbial Growth Modification by Compressed Gases and Hydrostatic Pressure", Environmental Microbiology, Apr. 1984, pp. 780–787.
Fenn et al., "Growth of Streptococcus Faecalis Under High Hydrostatic Pressure and High Partial Pressures of Inert Gases", Jour. of Gen. Physiology, 1968, vol. 52, pp. 810–824.
Davidson et al., "Effects of Elevated Pressures on Iron- -and Sulfur-Oxidizing Bacteria", Biotech, Bioeng. Symp., 1981, No. 11, 603–618.
Taylor, "Growth of a bacterium Under a High-Pressure Oxy-Helium Atmosphere", Applied and Environmental Microbiology, Jan. 1979, vol. 37, No. 1, pp. 42–49.
Sternberg, "A Method for Increasing Cellulase Production by Trichoderma Viride", Biotech. Bioeng., 1976, vol. 18, pp. 1751–1760.
Sturm et al., "Growth of the Extreme Thermophile Sulfolobus Acidocaldarius in a Hyperbaric Helium Bioreactor", Submitted to Biotech. Bioeng., (Feb. 1986), Revised Apr. 1986.
Sturm et al., "Growth of Extremely Thermophilic Archaebacteria Under Elevated Hyperbaric Conditions", Submitted to Ann. N.Y. Acad. Sci. (Sep. 1986).
Zobell et al., "Growth, Reproduction, and Death Rates of Escherichia Coli at Increased Hydrostatic Pressures", J. Bacteriol, 1962, vol. 84, pp. 1228–1236.

*Primary Examiner*—Robert A. Wax
*Attorney, Agent, or Firm*—Senniger, Powers, Leavitt and Roedel

[57] ABSTRACT

A process for producing enzyme cellulases by the fermentation of *Trichoderma reesei* in an aqueous nutrient medium containing assimilable sources of cellulose, nitrogen, phosphate, magnesium and iron in the presence of an oxygen containing atmosphere and a fermentation apparatus for the aerobic fermentation of microorganisms in a liquid medium at a pressure in excess of about 7 atmospheres. The method comprises fermenting the *Trichoderma reesei* at a temperature of between about 26° C. and 31° C. while maintaining the oxygen containing atmosphere at a pressure of about 1 atmosphere until the *Trichoderma reesei* enter the late stationary growth phase, thereafter, gradually and steadily increasing the pressure of the oxygen containing atmosphere until it is in excess of about 7 atmospheres and culturing the *Trichoderma reesei* at said increased pressure and at a temperature of between about 40° C. and about 60° C., thereby resulting in the production of enzyme cellulases by the *Trichoderma reesei*, and recovering the enzyme cellulases.

6 Claims, 3 Drawing Sheets

FERMENTATION OF TRICHODERMA REESEI AND APPARATUS THEREFOR

BACKGROUND OF THE INVENTION

This invention relates to a process for producing enzyme cellulases by the fermentation of *Trichoderma reesei* (ATCC 26921) at elevated pressures and temperatures and an apparatus for high pressure fermentation.

A considerable quantity of cellulosic wastes and residues are continuously generated in the U.S. and elsewhere. For pollution abatement reasons and because these wastes represent an inexpensive source of biomass, it would be desirable to convert these cellulosic wastes into useful products. One proposal has been to convert cellulose in these wastes and residues into glucose by enzymatic hydrolysis.

A known source of enzymes that hydrolyse cellulose is *Trichoderma reesei* (ATCC 26921), a green mold. When fermented in a culture medium comprising a source of cellulose, this microorganism produces a potent extracellular complex of cellulolytic enzymes, e.g., Filter Paper (FP) cellulase, CMC cellulase and glucosidase, capable of effectively hydrolyzing crystalline cellulose to glucose. However, because a large amount of enzyme is needed, this method is only commercially practical if a relatively low cost method exists for the production of the enzyme.

Presently, most commercially significant fermentation processes are carried out in a batchwise manner under one atmosphere of pressure and at a temperature between 25° C. and 60° C. Such processes typically require days to complete, and the low yields and slow productivity are always under the constant threat of contamination. Moreover, such methods require a continuous supply of air and vigorous agitation in order to supply sufficient oxygen to the microorganisms.

In order to improve the productivity, efforts have been made to develop optimum strains of certain microorganisms (including *T. reesei*) using processes of mutation and selection. Although offering promise, these attempts have not provided a relatively inexpensive source of enzyme.

SUMMARY OF THE INVENTION

Among the several objects of the invention, therefore, may be noted the provision of an improved process for the production of enzymatic cellulases by fermentation of *T. reesei* (ATCC 26921); the provision of such a process which accelerates bioconversion; the provision of such a process which increases enzyme production; and the provision of such a process which reduces the period of time necessary to complete the bioconversion thereby reducing the threat of contamination. Further objects of the invention include the provision of an apparatus useful and effective for the production of enzyme cellulases by the process of the present invention.

Briefly, therefore, the present invention is directed to a process for producing enzyme cellulases by the fermentation of *Trichoderma reesei* (ATCC 26921) in an aqueous nutrient medium containing assimilable sources of cellulose, nitrogen, phosphate, magnesium and iron in the presence of an oxygen containing atmosphere. The method comprises fermenting the *Trichoderma reesei* at a temperature of between about 26° C. and 31° C. while maintaining the oxygen containing atmosphere at a pressure of about 1 atmosphere until the *Trichoderma reesei* enter the late stationary growth phase, thereafter, gradually and steadily increasing the pressure of the oxygen containing atmosphere until it is in excess of about 7 atmospheres and culturing the *Trichoderma reesei* at said increased pressure and at a temperature of between about 40° C. and about 60° C., thereby resulting in the production of enzyme cellulases by the *Trichoderma reesei*, and recovering the enzyme cellulases produced by the *Trichoderma reesei*.

The invention is further directed to a fermentation apparatus for the aerobic fermentation of microorganisms in a liquid medium at a pressure in excess of about 7 atmospheres. The fermentation system comprises a fermentation vessel, an oxygen containing atmosphere line connected to an inlet port of the fermentation vessel, an atmosphere outlet line connected to an outlet port of the fermentation vessel, and a recycle loop. The fermentation vessel has stirrer means, cooling means, means for controlling the pH of the liquid medium, a sparger, an oxygen containing atmosphere inlet port connected to the sparger, and an atmosphere outlet port. The oxygen containing atmosphere line connected to said inlet port comprises a compressor for compressing the oxygen containing atmosphere to a pressure in excess of 7 atmospheres, at least one accumulator in communication with said compressor for containing a quantity of compressed oxygen containing atmosphere, a sterilizer for sterilizing the compressed oxygen containing atmosphere prior to its introduction to the fermentation vessel, and a metering valve between said accumulator and said vessel. The atmosphere outlet line connected to the outlet port comprises a condenser for condensing any condensables from the atmosphere that exits the vessel via said outlet port and a pressure controller for maintaining the pressure of the atmosphere within said condenser. The recycle loop comprises an inlet in communication with the fermentation vessel at a point below the surface of the liquid medium, a recycle pump, a recycle vessel having pH electrodes for analysis of liquid medium transferred to the recycle vessel by the recycle pump, and an outlet in communication with the fermentation vessel for the return of liquid medium from the recycle vessel to the fermentation vessel.

Other objects and features will be in part apparent and in part pointed out hereinafter.

DESCRIPTION OF THE PREFERRED EMBODIMENTS

Figure 1:
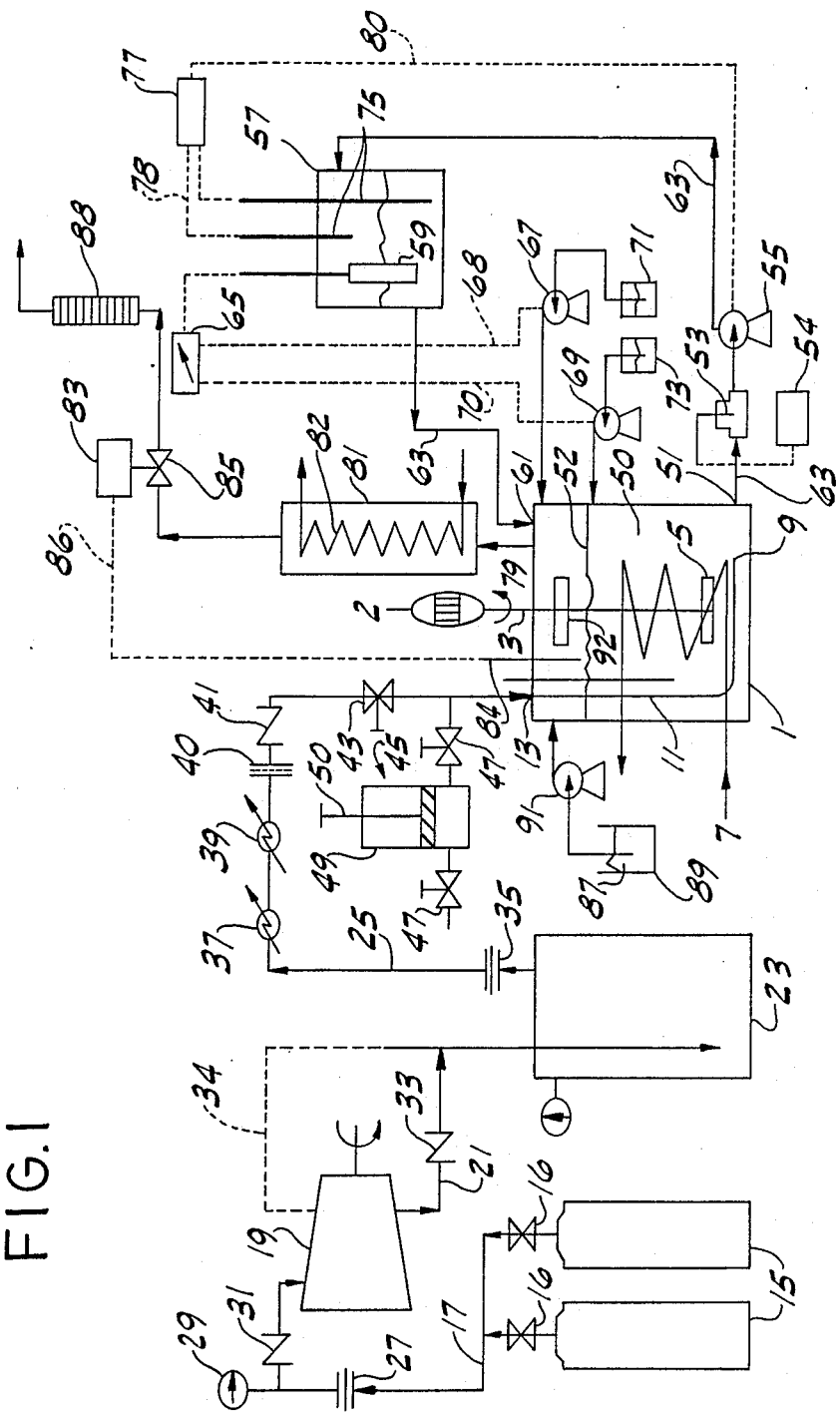
FIG. 1 is a Schematic diagram of the high pressure fermentation apparatus of the present invention.

In accordance with the present invention, it has been discovered that fermentation of *T. reesei* (ATCC 26921) at elevated pressures and at elevated temperatures not only enhances the biochemical reaction rates in the cells, but also increases product formation. In particular, it has been found that fermentation of *T. reesei* (ATCC 26921) at a pressure in excess of about 7 atmospheres and a temperature between about 40° C. and 60°

C. significantly increases the production of enzyme cellulases.

As noted above, it was known prior to the present invention that *T. reesei* produces enzyme cellulases when fermented in a media containing assimilable sources of cellulose, nitrogen, and phosphate in the presence of an oxygen containing atmosphere. According to those previously known processes, the preferred temperature and pressure for the fermentation were approximately 30° C. and 1 atmosphere, respectively.

When grown under such conditions, four growth phases of *T. reesei* are readily recognizable: (1) the lag phase, in which there is no rise in the number of viable cells; (2) the log phase, in which the cell population increases logarithmically or exponentially with time; (3) the stationary phase, in which the total number of viable cells remains constant; and (4) the death phase, which is characterized by an exponential decrease in the number of viable cells. Moreover, there is a relationship between the growth phase and the pH. After the culture is placed in fresh medium (pH 5.95), it remains in the lag phase for approximately one day. Thereafter, it enters the log phase and the cells divide at their maximum rate. As the cell number increases, the media pH begins to decrease. For optimum growth, the media pH is not allowed to go below 3.5. After about three to four days of growth, the microorganism reaches the stationary phase and the cell number no longer increases. In the stationary phase, the media pH begins to rise. About two days after entering the stationary phase, the media pH rises to about 4.4 and this portion of the stationary phase (after the pH rises to about 4.4) is known as the late stationary phase. The late stationary stage persists for approximately one to two days with the media pH increasing to about 5.25. Thereafter, the onset of the death phase drastically reduces the number of cells in the media.

In accordance with the process of the present invention, it has been discovered that the stationary phase can be extended and greater quantities of enzyme cellulases produced if the temperature and pressure of the media are increased during the late stationary phase. Thus, fermentations are preferably started at one atmosphere pressure and carried out until the *T. reesei* (ATCC 26921) population reaches the late stationary phase (approximately 2 days after the cell population becomes constant and characterized by an increase in the pH to about 4.4). At that point, the pressure in the fermentation vessel is gradually increased (preferably at a rate between about 20–70 psi/min.) and the temperature is controlled so that it does not exceed about 50° C. After the set point pressure (preferably in excess of about 7 atmospheres, and most preferably between about 117 and 127 atmospheres) and set point temperature (preferably between 40° C. and 60° C., and most preferably about 45° C.) are reached, fermentation continues until the population enters the death phase. Thereafter, the vessel is depressurized, the cells lysed and the enzyme cellulases are recovered.

The aqueous media used for fermentation of *T. reesei* under atmospheric conditions is suitable for high pressure fermentation of *T. reesei* in accordance with the present invention. Such a media is disclosed in Mandel and Reese, *J. Bacteriol.* 73,269 (1957). A preferred salt medium for high pressure fermentation comprises ammonium sulfate (1.4 gm/l), urea (0.3 gm/l), potassium biphosphate (2.0 gm/l), magnesium sulfate (0.3 gm/l), calcium chloride (0.3 gm/l) and trace amounts of iron (1 ppm), zinc (0.8 ppm), manganese (0.5 ppm) cobalt (0.5 ppm) and molybdenum (1 ppm). The trace metals are preferably provided from the following compounds: $FeSO_4 \cdot 7H_2O$, $ZnCl_2$, $MnSO_4 \cdot H_2O$, $CoCl_2 \cdot 6H_2O$, and $20MoO_3 \cdot 2H_3PO_4 \cdot 48H_2O$.

Fermentation of *T. reesei* must be carried out in the presence of an atmosphere which contains oxygen, i.e., an oxygen containing atmosphere. Preferably, the atmosphere contains between 6 and 12 per cent oxygen (most preferably 10 per cent oxygen) and a balance of nitrogen or helium.

Depicted in FIG. 1 is an apparatus suitable for carrying out the process of the present invention. The apparatus comprises a fermentation vessel 1 which is a modified 3.7-liter (i.d.: 0.127 m, o.d.: 0.181 m, internal height: 0.305 m) pressure vessel purchased from Autoclave Engineers (Erie, PA). All materials that are to be in contact with liquid substances are made of stainless steel 316. The fermentation vessel 1 is rated up to 370 atm at 340° C., has baffles (not shown) and a bolted closure (not shown). It has a two stage marine propeller-type agitator 2, driven magnetically in a controllable speed range up to 2500 rpm, having stirrer shaft 3 with a pitched blade 5. Cooling and heating of the vessel are provided by a coil 7 through which heating or cooling fluids are passed. A sparger 9, 28 cm long with 5 holes (each 1.5 cm apart) is located about 4 cm. below the pitched blade 5 and is connected via tube 11 to oxygen containing atmosphere inlet port 13. Also connected to the oxygen containing inlet port 13 is a source of oxygen containing atmosphere comprising gas reserve bottles 15 connected via tube 17 to compressor 19 which is connected via tube 21 to accumulator 23 which is connected to the oxygen containing atmosphere inlet port 13 via tube 25.

Located between gas reserve bottles 15 and compressor 19 along the length of tube 17 are valves 16, 10-micron filter 27, pressure gauge 29 and check valve 31. Located between compressor 19 and accumulator 23 along the length of tube 21 is check valve 33. Dotted lines 34 designate a control system for compressor 19. Located between accumulator 23 and the oxygen containing atmosphere inlet port 13 are 2-micron filter 35, electrical heater sterilizer 37, cooler 39 for returning the sterilized atmosphere to room temperature, 0.2-micron filter 40, check valve 41 and metering valve 43. Also located between accumulator 23 and oxygen containing atmosphere inlet port 13 is sampling device 45 which comprises metering valves 47 and container 49 having plunger 50. The sampling device 45 is designed for the withdrawal of samples from the fermentation vessel at a rate of 10 ml/min. Each of the pieces of equipment located between the compressor 19 and the oxygen containing atmosphere inlet port 13 is capable of withstanding pressures of 340 atmospheres.

For measurement of pH and oxygen content of the liquid medium 50 contained within the fermentation vessel 1, there is a recycle loop comprising recycle loop inlet 51 connected to the fermentation vessel 1 near the bottom thereof and well below liquid medium surface 52, oxygen probe 53 (contained within a "T" as shown in FIG. 1) and oxygen probe meter 54, recycle pump 55, recycle vessel having pH electrodes 59, and recycle loop outlet 61 which connects to the fermentation vessel 1, all capable of withstanding pressures of up to 340 atmospheres. Connecting each of the aforementioned elements of the recycle loop is tubing 63. The oxygen probe 53 is a model SBE 13 purchased from Seabird Electronics, Inc. (Bellovue, WA) and the pH electrode 59 is a combination-type pH electrode purchased from Innovative Sensor, Inc. (Anaheim, CA). The recycle pump 55 is a high pressure diaphragm pump model ELM-1 purchased from American Lewa (Natick, MA); use of a diaphragm pump is superior to a piston pump which may grind or otherwise destroy microorganisms contained within the fermentation media.

The recycle loop is adapted for continuous analysis of the pH and oxygen content of the liquid medium 50 during fermentation. A quantity of the liquid medium 50 is transferred to the oxygen probe 53 where the oxygen content is measured and shown on oxygen probe meter 54 and then transferred to recycle vessel 57 by means of recycle pump 55. There, the liquid medium is analyzed for pH by electrodes 59 and recorded on recorder controller 65. If the pH of the liquid medium is too high or too low, controller 65 activates either base pump 67 or acid pump 69, via electrical connections 68 and 70 to pump the necessary quantity of base from base reservoir 71 or the necessary quantity of acid from acid reservoir 73 into the fermentation vessel 1.

In addition to pH electrodes 59, the recycle vessel 57 additionally contains level probes 75 which are connected to level controller 77 via electrical connections 78. Level controller 77 measures the quantity of medium within the reaction vessel 57 and activates recycle pump 55 by means of electrical connection 80 as necessary to maintain the desired level.

Exhausted oxygen containing atmosphere in the fermentation vessel 1 exits the vessel through atmosphere outlet port 79. To minimize the loss of liquid medium and any condensables from the fermentation vessel, the exhausted atmosphere is passed through condenser 81 after exiting through the outlet port 79. Pressure controller 83 monitors the pressure within the fermentation vessel by means of pressure sensor 84 which is electrically connected (as shown by dotted lines 86) to the pressure controller 83. The pressure controller 83 operates a gear driven, pressure-control valve 85 to maintain the proper pressure within the condenser 81 and fermentation vessel 1. After passing through valve 85, the exiting atmosphere passes through a rotameter type flow meter 88 and then out of the apparatus and piped to an incinerator (not shown). Cooling water flows through coils 82 of condensor 81 to condense moisture and any condensables from the atmosphere which exits the fermentation vessel 1.

To minimize the formation of foam during the fermentation process, an antifoam agent 87 is contained within antifoam vessel 89 and pumped into the fermentation vessel 1 by pump 91 as necessary. A suitable antifoam agent is a 10% silicone-based antifoam agent sold under the product designation A5633 by Sigma Chemical Company (St. Louis, MO). Also for the purpose of reducing foam within the fermentation vessel is a mechanical foam breaker 92 near the top of the stirrer shaft 3 within the fermentation vessel 1.

OPERATION

Liquid medium containing *T. reesei* (ATCC 26921) fermented at atmospheric pressure in a conventional fermentation vessel is transferred to the fermentation apparatus of the present invention when the microorganism population enters the late stationary phase of growth. Oxygen containing atmosphere (1 to 20% $O_2$ in $N_2$) from gas reserve bottles 15 is fed to the fermentation vessel through the sparger 9. Oxygen depleted atmosphere is removed from the fermenation vessel through atmosphere outlet port 79 with any moisture carried by the depleted atmosphere being captured by the condenser 81 and returned to the fermentation vessel.

Immediately after the liquid medium containing *T. reesei* is transferred to the fermentation vessel, the pressure is gradually increased, i.e., the pressure is increased at a rate of 340 KPa (50 psi) per minute until it reaches the desired pressure. By isolating the compressor from the fermenation vessel, the accumulators serve to reduce unwanted pressure fluctuations caused by the compressor by operating as follows: after the pressure of the oxygen containing atmosphere contained within the first accumulator is raised to a specified level, the system is switched so that the compressor is now filling the second accumulator while the first accumulator is emptying its contents into the fermentation vessel. The cycle is continuously repeated to provide fresh oxygen containing atmosphere to the fermentation vessel. The pressure in the vessel is increased until the set point pressure is reached. As noted above, for *T. reesei* it is preferred that the set point pressure be above 7 atmospheres and most preferably in the range of 117 to 127 atmospheres.

Throughout the fermenation process, the fermentation vessel contents are thoroughly mixed by the two-stage, magnetic driven stirrer 3 and the temperature of the fermentation vessel contents is controlled through the use of coil 7. Cooling and heating fluids are passed through the coil 7 as necessary so that the temperature for the *T. reesei* containing medium is maintained between about 40° C. and 60° C. (when the contents are at a pressure in excess of 7 atmospheres).

To continuously monitor the pH and oxygen content of the fermentation medium, recycle pump 55 continuously withdraws the liquid medium to feed recycle vessel 57 where pH electrodes are installed; the fermentation medium returns to the fermentation vessel by gravity. A level controller 77 attached to the recycle vessel controls the speed of the recycle pump in order to prevent the liquid from over-filling, which may damage the pH electrodes 59. If the pH of the medium exceeds or is below the desired level, controller 65 activates either base pump 67 or acid pump 69 to pump the necessary quantity of base from base reservoir 71 or the necessary quantity of acid from acid reservoir 73 into the fermentation vessel 1. Suitable acid and base pumps include high pressure pumps sold e.g., the model AA-94 high pressure pump sold by Eldex Laboratories Inc. (San Carlos, CA).

The following examples illustrates the invention.

EXAMPLE 1

High Pressure Fermentor

The high pressure fermentor used is shown in FIG. 1 and described in detail above.

Preparation of Gas Mixture

The high pressure gas mixture had a composition of 10% $O_2$ in $N_2$. The mixture was prepared by blending two ultra pure grade gases to a 42-liter high pressure gas bottle by a diaphragm compressor (Fluitron model A1-700, Fluitron Inc., Ivyland, PA). The gas bottle collected up to 400 atm of compressed gas mixture from which continuous supply of the gas to the fermentor was made by a regulator. The gas composition was expressed in mole-percent, assuming that the mixture behaves as an ideal gas. The gas mixture entering the fermentor was sterilized by an electrical heater maintained at 250° C. and it was cooled to an ambient temperature before passing through a 0.2-micron filter.

Culture

Stock cultures of *Trichoderma reesei* (ATCC 26921) were maintained at 25° C. on potato dextrose agar slants. The salt medium employed for both atmospheric and high pressure fermentation was the one developed by Mandel and Reese (J. Bacteriol. 73: 269, 1957). A food-grade wood cellulose, Solka Floc SW40 (Jame River Corporation, Hackensack, NJ), having an average fiber length of 120 microns, was used as a carbon source.

Low Pressure Fermentation

Fermentations at one atmosphere pressure and 28° C. were carried out in a 20-liter fermentor (Microgen Model 20, New Brunswick Scientific, Edison, NJ) with a pH control system and an oxygen monitoring unit. A 10% NaOH solution was used for the PH control, as well as 10% silicon-based antifoam (Sigma Chemicals, Product A5633, St. Louis, MO), diluted with deionized water, which was employed to suppress the foaming during fermentation. Throughout this study 0.75 grams of cellulose were used in the culture. The air flow rate of 4 liters per minute with 10 liters of medium (0.4 VVM) and an agitation rate at 250 rpm were maintained during the atmospheric pressure fermentation. The initial spore concentration, after innoculation, was always maintained at 500,000 spores per ml.

High Pressure Fermentation

For high pressure fermentation, 2 liters of the cells grown at one atmosphere at various growth phases (as indicated in the Figures described below) were asceptically transferred to the high pressure fermentor and the vessel was pressurized at a rate of 2 atm per minute until the final desired pressure was obtained. The desired temperature was achieved by the fermentation vessel heating and cooling coil. Sampling from the high pressure fermentor was carried out by a plunger-type sampling device at a flow rate of 5 ml per minute. The oxygen containing atmosphere (10% $O_2$ in $N_2$ was 0.25 VVM (volume of gas mixture per volume of fermentation medium per minute) and the agitation rate was 180 rpm.

Analytical Methods

All the enzyme activities were expressed as units per ml of the culture medium, as determined by the number of milimoles of glucose (or, equivalent to glucose when measured by the Dinitrosalycilic method for reducing sugars) produced per minute, in pH 4.8, 0.05M acetate buffer. The enzymatic method of glucose oxidase for $\beta$-glucose and the Lowry's method for protein were employed in the study. An indirect method for the estimation of the cell growth in the culture broth was employed by measuring the amount of extracellular protein present in supernatent liquid, after centrifuging culture samples withdrawn from the fermentor, at 5° C. for 10 minutes at 2000 rpm (DuPont's Sorvall Instrument Model RC5C).

Results

Figure 2:
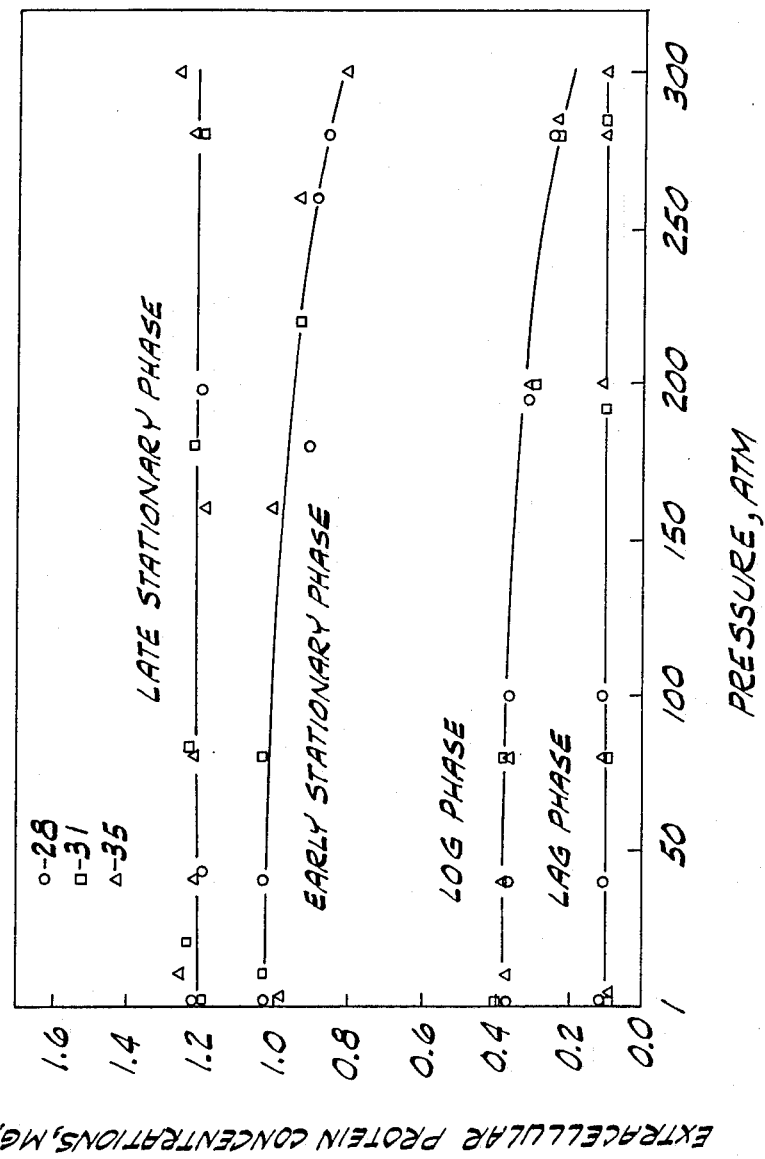
FIG. 2 is a graph showing the effect of temperature and pressure upon the growth of *T. reesei* populations under the conditions described in Example 1.

FIG. 2 shows the effect of pressures greater than 1 atmosphere and temperatures of 28° C., 31° C. and 35° C. on the growth of the cells transferred to the high pressure fermentation vessel at the indicated age (lag, exponential (log), early stationary and late stationary phases). For pressures greater than 1 atmosphere, the extracellular protein levels reported in FIG. 2 represent an average of the protein levels in the medium at the time the transfer to the high pressure vessel was made, one day later and two days later; for a pressure of one atmosphere, the protein levels reported in FIG. 2 represent the protein level for the cell population at the indicated growth stage fermented at 28° C. The results demonstrate that fermentation at pressures of between 122 and 300 atmospheres and temperatures of 28° C., 31° C. and 35° C. inhibit the growth of the cells transferred to the high pressure fermentation vessel during the exponential (log), and early stationary growth stages as compared to atmospheric fermentation. This inhibition, however, is not seen by the cells transferred to the high pressure fermentation vessel during the late stationary phase and lag phases, indicating relative insensitivity of cells transferred in these phases to the elevated pressures between 122 and 300 atm (FIG. 2).

Figure 3:
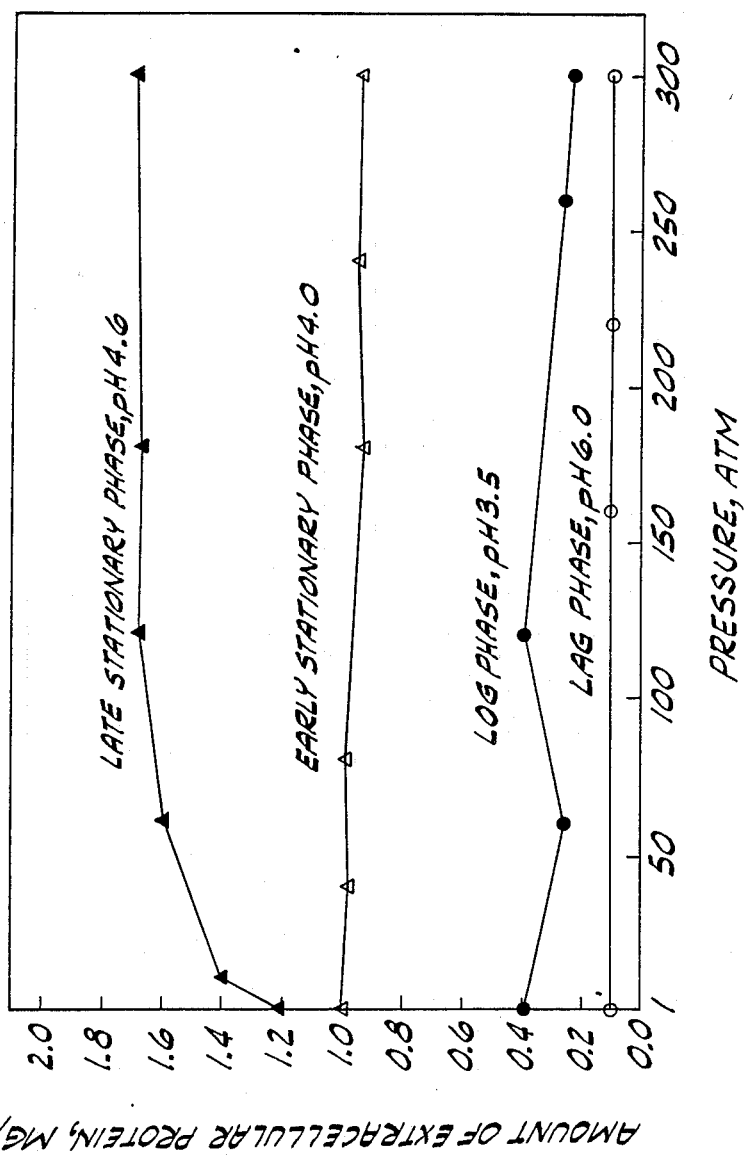
FIG. 3 is a graph showing the effect of temperature and pressure upon the growth of *T. reesei* populations under the conditions described in Example 1.

FIG. 3 shows the effects of a temperature of 44.8° C. and pressures in excess of 1 atmosphere on the growth and the product formation of the enzyme cellulases by cells transferred to the high pressure fermentor at the indicated age. Again, for pressures greater than 1 atmosphere, the extracellular protein levels reported in FIG. 3 represent an average of the protein levels in the medium at the time the transfer to the high pressure vessel was made, one day later and two days later; for a pressure of one atmosphere, the protein levels reported in FIG. 3 represent the protein level for the cell population at the indicated growth stage fermented at 28° C. In contrast to that shown in FIG. 2, an increase in protein synthesis was clearly seen from the cells transferred in the late stationary phase. At around 122 atmospheres the protein synthesis had reached its maximum level of 1.7 mg/ml, maintaining this level at variable pressures up to 300 atm. An increase, up to 35%, in protein synthesis was noted at 44.8° C. and at pressures between 122 and 300 atm as compared to cells fermented at 1 atmosphere pressure and 28° C.

EXAMPLE 2

Using the apparatus and procedure of Example 1, a cell culture was fermented at 31° C. (Air at 0.4 VVM) and atmospheric pressure in a low pressure fermentor until the cell population reached the late stationary stage (day 6). At that point, a portion of the medium was transferred to the high pressure fermentor and the cells grown at 44.8° C. (10% $O_2$ in $N_2$ at 0.25 VVM) for 11 additional days while the remaining portion of the medium remained in the low pressure fermentor and was grown for 4 additional days. Samples of from the low pressure and high pressure fermentor were analyzed for protein content and enzyme activity as outlined in Example 1 and the results are presented in Table 1.

The results presented in Table 1 demonstrate that an increase of protein synthesis of approximately 30 to 40% is observed when the cells in the late stationary phase were brought into a new culture condition of the elevated pressure and temperature as compared to cells grown at atmospheric pressure and 31° C. The increase of the three enzyme activities are also seen from this table, although their degrees of increase vary. The order of increases in enzyme activity and the percentages in activity increase were as follows:

1.) FP-cellulase, 35%
2.) B-Glucosidase, 5%
3.) CMC-cellulase, 4%

TABLE I

PROFILES OF PROTEIN CONCENTRATIONS AND ENZYME ACTIVITIES DURING 9 DAY OF FERMENTATION

| DAY | pH | PROTEIN (mg/ml) | FP ACTIVITY | CMC ACTIVITY | GLUCOSIDASE |
|---|---|---|---|---|---|
| Low Pressure | | | | | |
| 1 | 5.90 | 0.00 | 0.00 | 0.00 | 0.00 |
| 2 | 4.25 | 0.035 | 0.148 | 0.371 | 0.002 |
| 3 | — | — | — | — | — |
| 4 | 3.50 | 0.496 | 0.153 | 0.834 | 0.125 |
| 5 | 3.49 | 1.095 | 0.266 | 0.979 | 0.178 |
| *6 | 4.20 | 1.355 | 0.349 | 0.957 | 0.089 |
| 7 | — | — | — | — | — |
| 8 | 7.10 | 1.455 | 0.302 | 0.991 | 0.263 |
| 9 | 6.60 | 1.405 | 0.373 | 1.083 | 0.403 |
| 10 | 6.84 | 1.421 | 0.295 | 1.051 | 0.342 |
| High Pressure | | | | | |
| *1 | 4.20 | 1.335 | 0.349 | 0.957 | 0.089 |
| 2 | — | — | — | — | — |
| 3 | 3.66 | 2.041 | 0.285 | 0.968 | 0.315 |
| 4 | 3.59 | 1.967 | 0.336 | 1.015 | 0.332 |
| 5 | — | — | — | — | — |
| 6 | 3.79 | 1.930 | 0.467 | 0.947 | 0.383 |
| 7 | — | — | — | — | — |
| 8 | 3.67 | 1.930 | 0.464 | 1.064 | 0.291 |
| 9 | — | — | — | — | — |
| 10 | — | — | — | — | — |
| 11 | 3.60 | 1.893 | 0.167 | 1.000 | 0.403 |

*Transfer of Medium from the Low (1 ATM.) Pressure to the High Pressure Fermentor In view of the above, it will be seen that the several objects of the invention are achieved and other advantageous results attained.

As various changes could be made in the above methods and products without departing from the scope of the invention, it is intended that all matter contained in the above description shall be interpreted as illustrative and not in a limiting sense.

What is claimed is:

1. A process for producing enzyme cellulases by the fermentation of *Trichoderma reesei* (ATCC 26921) in an aqueous nutrient medium containing assimilable sources of cellulose, nitrogen, phosphate magnesium and iron in the presence of an oxygen containing atmosphere, the method comprising fermenting the *Trichoderma reesei* at a temperature of between about 26° C. and 31° C. while maintaining the oxygen containing atmosphere at a pressure of about 1 atmosphere until the *Trichoderma reesei* enter the late stationary growth phase, thereafter, gradually and steadily increasing the pressure of the oxygen containing atmosphere until it is in excess of about 7 atmospheres and fermenting the *Trichoderma reesei* at said increased pressure and at an increased temperature of between about 40° C. and about 60° C., thereby resulting in the production of enzyme cellulases by the *Trichoderma reesei*, and recovering the enzyme cellulases.

2. A process as set forth in claim 1 wherein said aqueous nutrient medium comprises a source of calcium.

3. A process as set forth in claim 1 wherein said aqueous nutrient medium comprises trace amounts of manganese, cobalt, zinc and molybdenum.

4. A process as set forth in claim 1 wherein said increased pressure is between about 117 and about 127 atmospheres.

5. A process as set forth in claim 1 wherein said increased temperature is about 45° C.

6. A process as set forth in claim 4 wherein said increased pressure is about 122 atmospheres.

* * * * *